United States Patent
Provencher et al.

(10) Patent No.: US 10,478,379 B2
(45) Date of Patent: Nov. 19, 2019

(54) BIOLOGICAL SAMPLE CONTAINMENT SYSTEM AND LABEL

(71) Applicant: Becton, Dickinson and Company, Franklin Lakes, NJ (US)

(72) Inventors: Eric John Provencher, Edgewater, NJ (US); Craig Owen Russ, Wayne, NJ (US); Bo Yon Lillian Yoo, Ridgefield, NJ (US); Jamieson W. Crawford, Hagerten (SE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 516 days.

(21) Appl. No.: 14/755,224

(22) Filed: Jun. 30, 2015

(65) Prior Publication Data

US 2016/0015598 A1  Jan. 21, 2016

Related U.S. Application Data

(60) Provisional application No. 62/025,704, filed on Jul. 17, 2014.

(51) Int. Cl.
*A61J 1/00* (2006.01)
*G09F 3/02* (2006.01)
(Continued)

(52) U.S. Cl.
CPC ............. *A61J 1/00* (2013.01); *A61B 5/153* (2013.01); *A61B 5/15003* (2013.01);
(Continued)

(58) Field of Classification Search
CPC ...... A61J 1/00; A61B 5/150786; A61B 5/153; B01L 3/5453; B01L 2300/021;
(Continued)

(56) References Cited

U.S. PATENT DOCUMENTS

| 1,707,723 A | * | 4/1929 | Hulsebos | B60R 25/00 |
| | | | | 283/98 |
| 3,644,715 A | * | 2/1972 | Holderith | B01L 3/5453 |
| | | | | 235/442 |

(Continued)

FOREIGN PATENT DOCUMENTS

| JP | 2007535979 A | 12/2007 |
| JP | 2009526231 A | 7/2009 |

(Continued)

*Primary Examiner* — Ernesto A Grano
(74) *Attorney, Agent, or Firm* — The Webb Law Firm

(57) ABSTRACT

A biological sample containment system that includes a biological specimen collection container for collecting a biological sample and a label for the container is disclosed. In one embodiment, the label includes a first or front side and a second or rear side having a readable information portion. The label is affixable to the container by the second side and with the label affixed to the container, the readable information portion on the second side is readable through a portion of the container. By including readable information on the second or rear side of the label, the amount of readable information that can be included on the label is increased by using the previously unused rear side of the label.

15 Claims, 5 Drawing Sheets

(51) Int. Cl.
*G09F 3/00* (2006.01)
*G09F 3/10* (2006.01)
*G09F 3/20* (2006.01)
*B01L 3/00* (2006.01)
*A61B 5/15* (2006.01)
*A61B 5/153* (2006.01)

(52) U.S. Cl.
CPC ...... *A61B 5/150786* (2013.01); *B01L 3/5453* (2013.01); *G09F 3/02* (2013.01); *G09F 3/0297* (2013.01); *G09F 3/10* (2013.01); *G09F 3/203* (2013.01); *B01L 2300/021* (2013.01); *B01L 2300/022* (2013.01); *B01L 2300/0858* (2013.01); *G09F 2003/021* (2013.01); *G09F 2003/0216* (2013.01); *G09F 2003/0272* (2013.01)

(58) Field of Classification Search
CPC ....... B01L 2300/022; B01L 2300/0858; G09F 3/02; G09F 3/0297; G09F 3/10; G09F 3/203; G09F 2003/021; G09F 2003/0216; G09F 2003/0272
USPC .......................................................... 206/438
See application file for complete search history.

(56) References Cited

U.S. PATENT DOCUMENTS

| | | | | |
|---|---|---|---|---|
| 4,857,713 A | * | 8/1989 | Brown | A61B 5/117 235/375 |
| 5,030,341 A | * | 7/1991 | McEwen | B01L 3/50215 210/515 |
| 5,056,827 A | | 10/1991 | Sasso | |
| D432,174 S | * | 10/2000 | Stevens | D20/22 |
| D432,176 S | * | 10/2000 | Stevens | D20/22 |
| D432,245 S | * | 10/2000 | Stevens | D24/216 |
| D435,662 S | * | 12/2000 | Stevens | D20/22 |
| D435,663 S | * | 12/2000 | Stevens | D20/22 |
| D435,664 S | * | 12/2000 | Stevens | D20/22 |
| D436,182 S | * | 1/2001 | Stevens | D20/22 |
| D436,183 S | * | 1/2001 | Stevens | D20/22 |
| 6,272,777 B1 | | 8/2001 | Swenson | |
| 6,332,631 B1 | | 12/2001 | Kirk | |
| 6,637,775 B1 | | 10/2003 | Bernier et al. | |
| 6,676,794 B1 | | 1/2004 | Petkovsek | |
| 6,709,726 B1 | | 3/2004 | Dronzek, Jr. et al. | |
| 7,413,880 B2 | * | 8/2008 | Aki | G01N 33/558 422/412 |
| 7,740,411 B2 | | 6/2010 | Kaufman | |
| 8,043,463 B2 | | 10/2011 | Laaksonen et al. | |
| 8,357,442 B2 | | 1/2013 | Whittaker et al. | |
| 8,542,871 B2 | | 9/2013 | Voloshynovskiy et al. | |
| 8,609,211 B2 | | 12/2013 | Boucher et al. | |
| 8,894,951 B2 | * | 11/2014 | Wilkinson | A61B 10/0096 422/50 |
| 9,409,176 B2 | * | 8/2016 | Carano | A61B 5/1405 |
| 9,691,011 B2 | * | 6/2017 | Gelfand | G06K 19/06046 |
| 2001/0038204 A1 | | 11/2001 | Nojima et al. | |
| 2002/0050715 A1 | | 5/2002 | Elpidi | |
| 2003/0031598 A1 | * | 2/2003 | Stevens | B01L 3/5453 422/549 |
| 2003/0034645 A1 | | 2/2003 | Dronzek, Jr. et al. | |
| 2004/0075272 A1 | | 4/2004 | Kaufman | |
| 2005/0275213 A1 | | 12/2005 | Whitehouse et al. | |
| 2006/0133963 A1 | * | 6/2006 | Stein | B01L 3/5082 422/400 |
| 2008/0034628 A1 | | 2/2008 | Schnuckle | |
| 2008/0121688 A1 | * | 5/2008 | Harrop | G06K 19/06028 235/375 |
| 2010/0279397 A1 | | 11/2010 | Crawford et al. | |
| 2010/0327058 A1 | | 12/2010 | Schuller | |
| 2012/0180351 A1 | * | 7/2012 | Kalyankar | G09F 3/005 40/633 |
| 2015/0268215 A1 | * | 9/2015 | Tomellini | G01N 33/227 436/93 |
| 2015/0371008 A1 | * | 12/2015 | Kitao | G16H 10/40 235/380 |

FOREIGN PATENT DOCUMENTS

| | | |
|---|---|---|
| JP | 2013242246 A | 12/2013 |
| WO | 2007/092585 A2 | 8/2007 |

* cited by examiner

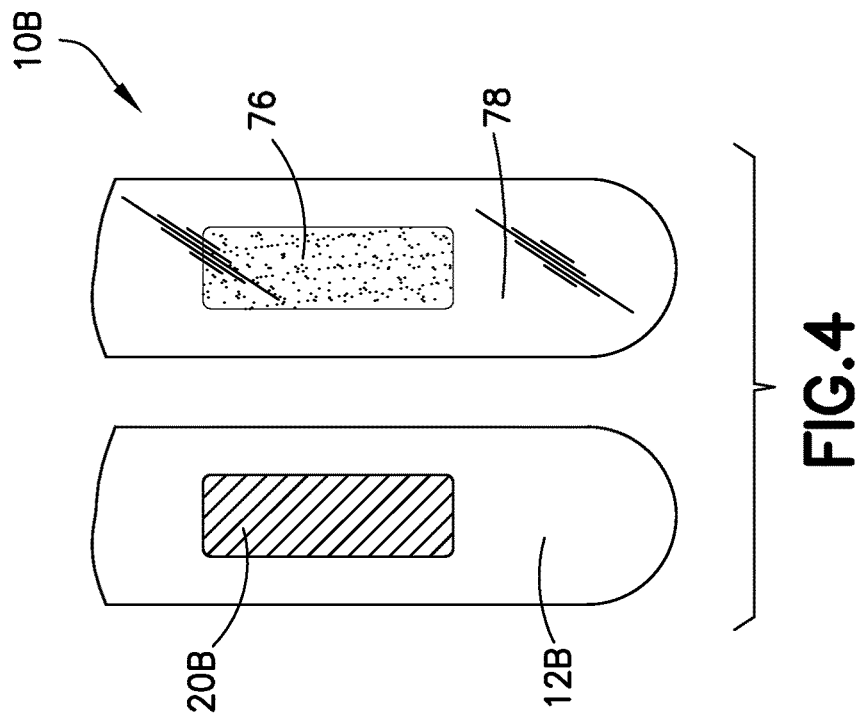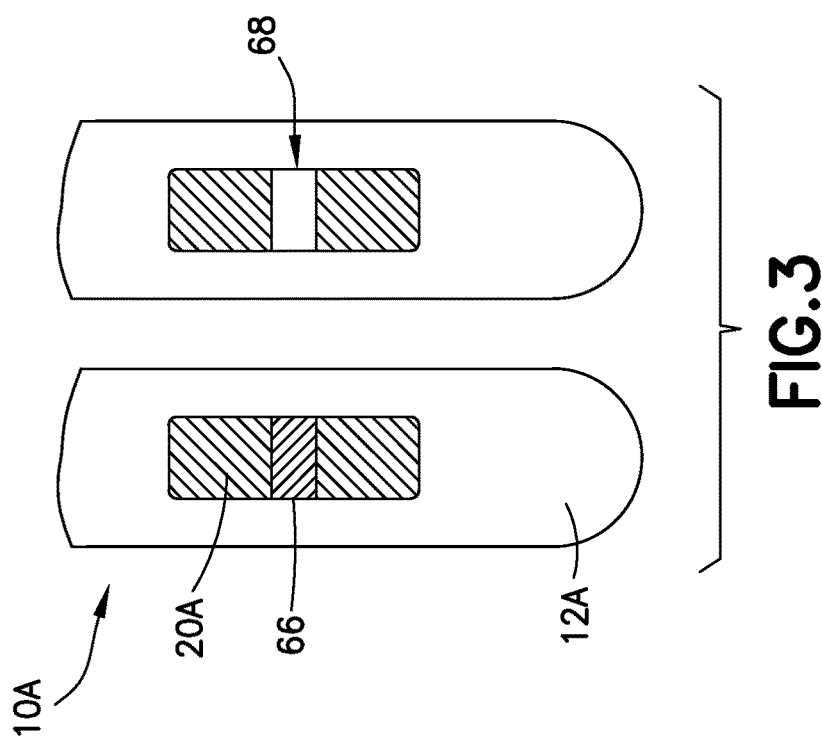

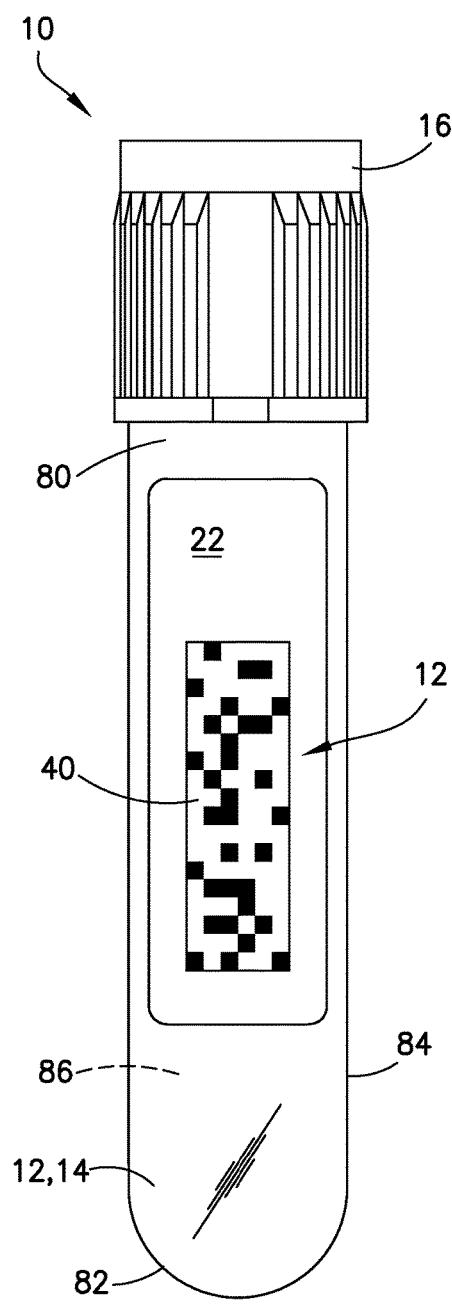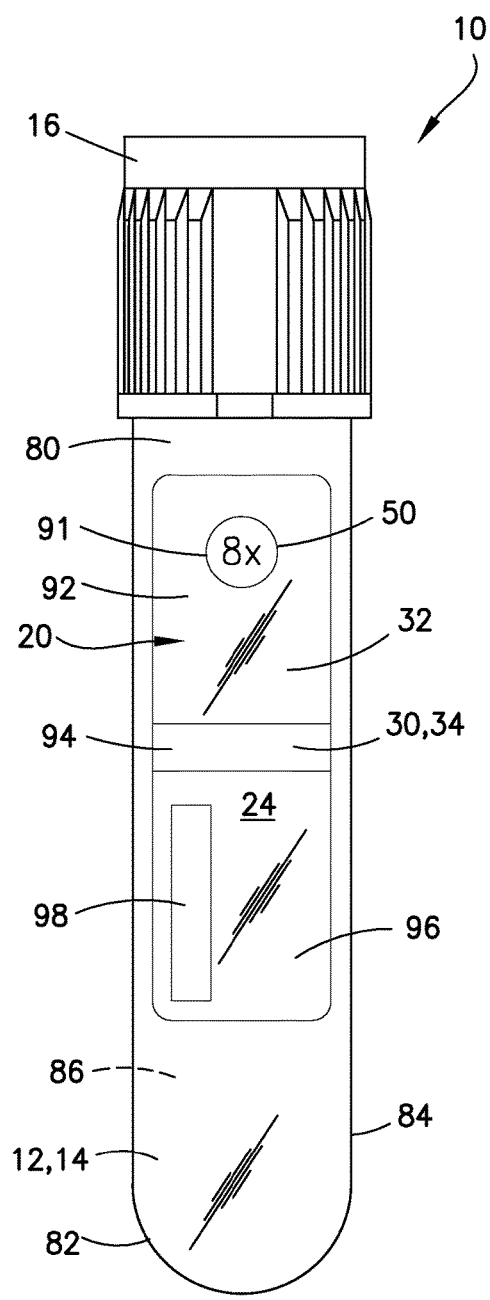

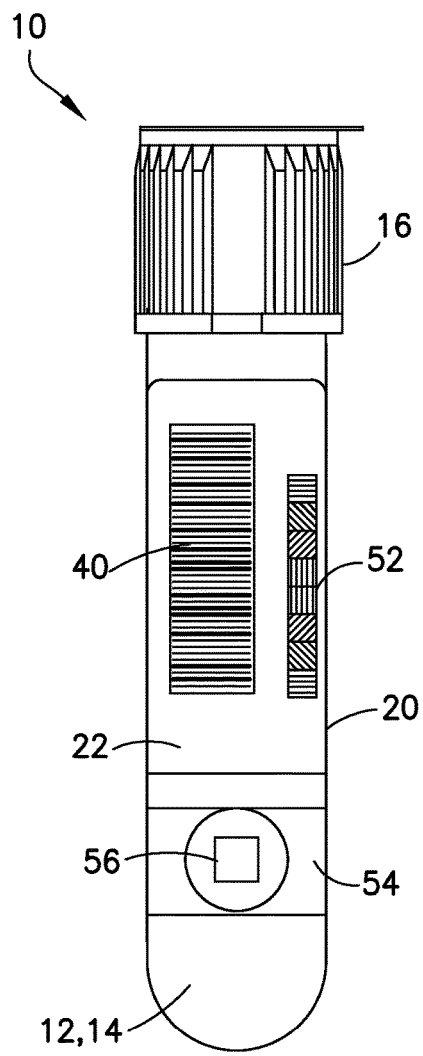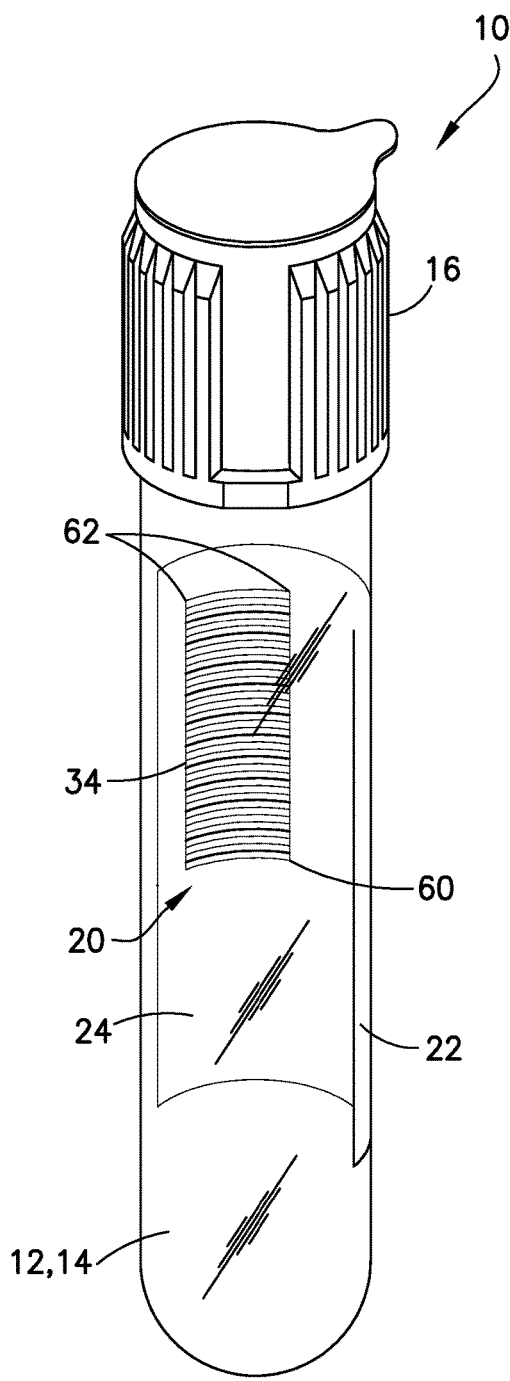
FIG.7
FIG.8

BIOLOGICAL SAMPLE CONTAINMENT SYSTEM AND LABEL

CROSS-REFERENCE TO RELATED APPLICATION

The present application claims priority to U.S. Provisional Application Ser. No. 62/025,704, entitled "Biological Sample Containment System and Label", filed Jul. 17, 2014, the entire disclosure of which is hereby incorporated by reference.

BACKGROUND OF THE INVENTION

1. Field of the Disclosure

The present disclosure relates generally to biological sample containment systems. More particularly, the present disclosure relates to systems for providing identifying information for biological sample containment systems.

2. Description of the Related Art

Biological sample collection containers, such as blood collection containers, are well-known in the medical arts. Biological sample collection containers are used to store a sample obtained by a healthcare professional from a patient until the sample is ready to be tested or used for other purposes.

When collecting biological samples in collection containers, it is often important that the container and/or sample are not exposed to a temperature that exceeds a certain threshold. In addition, it is sometimes important that the container is used within a certain timeframe upon manufacture, shipment, or some other event. In addition, it may be important to know the amount of time that has transpired after collection of the sample into the container.

Additionally, identifying other characteristics and/or information of the sample and/or container may be useful to the healthcare practitioner. For example, identifying the integrity of the sample, whether the sample has been subjected to appropriate procedures, e.g.; mixing, or whether the appropriate amount of sample has been collected may be significant.

SUMMARY OF THE INVENTION

The present disclosure provides a biological sample containment system that includes a biological specimen collection container for collecting a biological sample and a label for the container. In one embodiment, the label includes a first or front side and a second or rear side having a readable information portion. The label is affixable to the container by the second side and with the label affixed to the container, the readable information portion on the second side is readable through a portion of the container. Advantageously, by including readable information on the second or rear side of the label, the amount of readable information that can be included on the label is increased by using the previously unused rear side of the label.

In accordance with an embodiment of the present invention, a label for a container for collecting a biological sample includes a first side and a second side having a readable information portion, the label affixable to the container by the second side, wherein with the label affixed to the container, the readable information portion on the second side is readable through a portion of the container.

In one configuration, the second side includes a first readable information portion and a second readable information portion above the first readable information portion, wherein with the label affixed to the container, at least one of the first readable information portion and the second readable information portion is readable through a portion of the container. In another configuration, at least a part of the first readable information portion is a fill line indicator and at least a part of the second readable information portion is a barcode. In yet another configuration, at least a part of the readable information portion is a fill line indicator. In one configuration, at least a part of the readable information portion is a barcode. In another configuration, at least a part of the readable information portion comprises electronically readable information. In yet another configuration, at least a part of the readable information portion comprises, an inversion indicator. In one configuration, at least a part of the readable information portion comprises a hemolysis indicator. In another configuration, at least a part of the readable information portion comprises an order of draw indicator. In yet another configuration, the first side includes an outfacing readable information portion. In one configuration, at least a part of the outfacing readable information portion includes a time indicator. In another configuration, at least a part of the outfacing readable information portion includes a temperature indicator. In yet another configuration, at least a part of the outfacing readable information portion includes a hemolysis indicator. In one configuration, at least a part of the outfacing readable information portion comprises machine readable information. In another configuration, the first side is opposite the second side.

In accordance with another embodiment of the present invention, a biological sample containment system includes a container for containing a biological sample and a label capable of being affixed to the container, the label comprising a first side and a second side having a readable information portion, the label affixable to the container by the second side, wherein with the label affixed to the container, the readable information portion on the second side is readable through a portion of the container.

In one configuration, the second side includes a first readable information portion and a second readable information portion above the first readable information portion, wherein with the label affixed to the container, at least one of the first readable information portion and the second readable information portion is readable through a portion of the container. In another configuration, at least a part of the first readable information portion is a fill line indicator and at least a part of the second readable information portion is a barcode. In yet another configuration, at least a portion of the container is transparent. In one configuration, at least a part of the readable information portion is a fill line indicator. In another configuration, at least a part of the readable information portion is a barcode. In yet another configuration, at least a part of the readable information portion comprises electronically readable information. In one configuration, at least a part of the readable information portion comprises an inversion indicator. In another configuration, at least a part of the readable information portion comprises a hemolysis indicator. In yet another configuration, at least a part of the readable information portion comprises an order of draw indicator. In one configuration, the first side includes an outfacing readable information portion. In another configuration, at least a part of the outfacing readable information portion includes a time indicator. In yet another configuration, at least a part of the outfacing readable information portion includes a temperature indicator. In one configuration, at least a part of the outfacing readable information portion includes a hemolysis indicator. In another configuration, at least a part of the outfacing readable information portion comprises machine readable information.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 3 is elevation views of a biological sample containment system in accordance with another embodiment of the present invention.

FIG. 4 is elevation views of a biological sample containment system in accordance with another embodiment of the present invention.

FIG. 5 is a front elevation view of a biological sample containment system in accordance with another embodiment of the present invention.

FIG. 6 is a rear elevation view of a biological sample containment system in accordance with another embodiment of the present invention.

FIG. 7 is a front elevation view of a biological sample containment system in accordance with another embodiment of the present invention.

FIG. 8 is a perspective view of a biological sample containment system in accordance with another embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
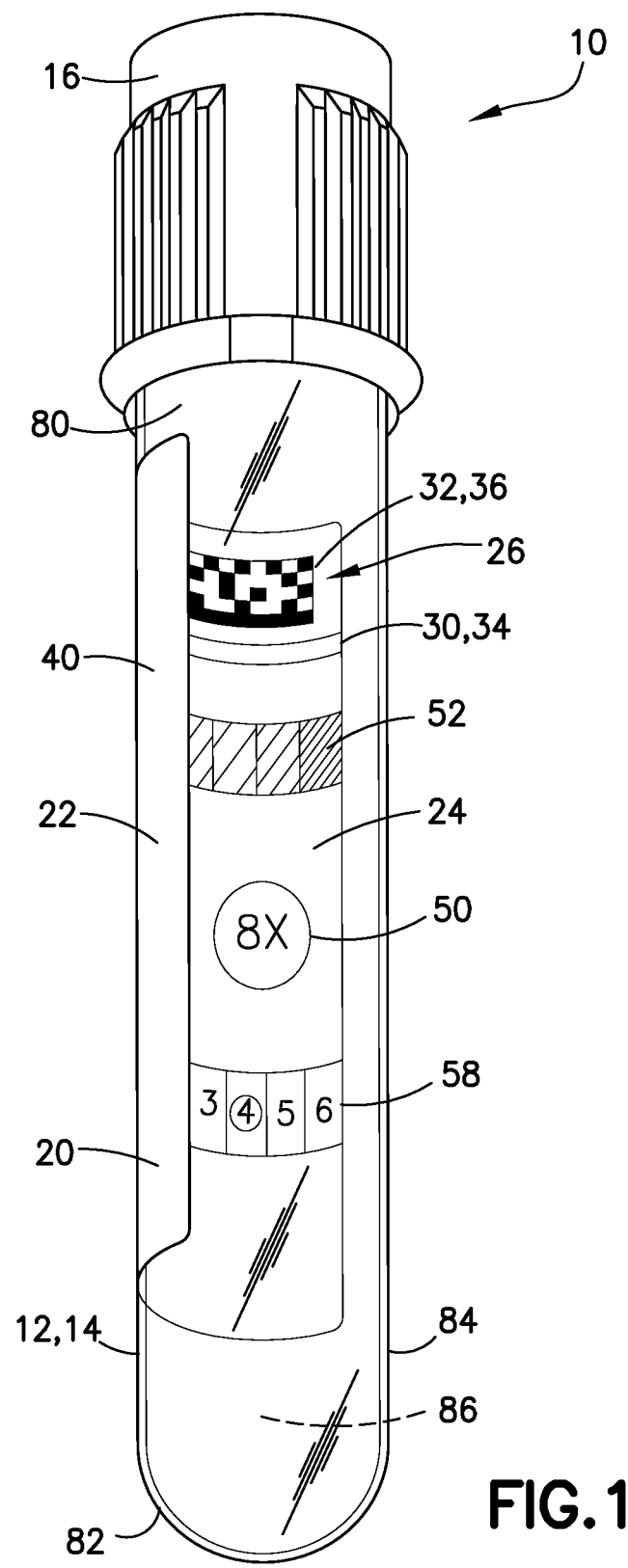
FIG. 1 is a perspective view of a biological sample containment system in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 2:
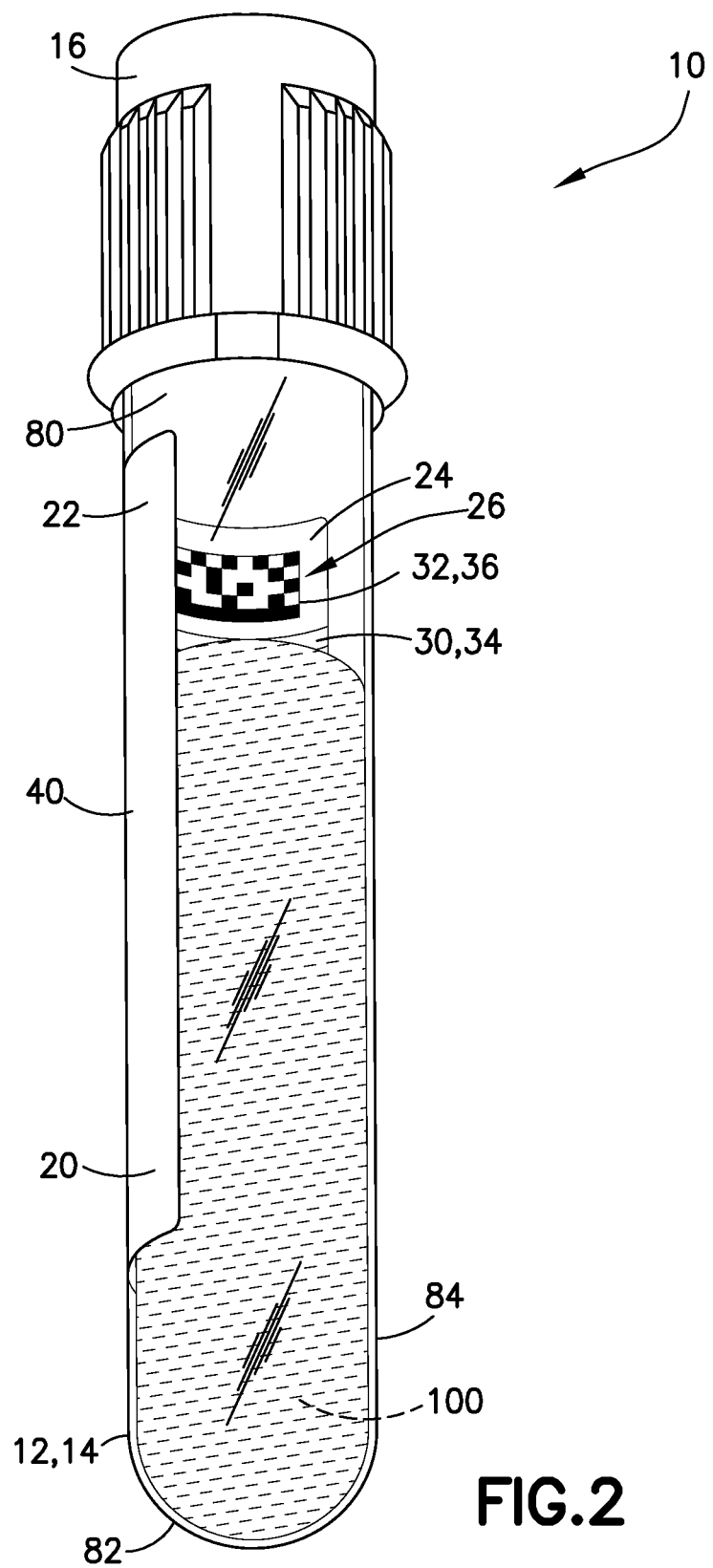
FIG. 2 is a perspective view of a biological sample containment system with a biological sample within a container in accordance with an embodiment of the present invention.

FIGS. 1 and 2 illustrate an exemplary embodiment of the present disclosure. Referring to FIGS. 1 and 2, a biological sample containment system 10 of the present disclosure includes a biological specimen collection container 12 for collecting a biological sample 100 (FIG. 2) and a labeling system or label 20 for the container 12. In one embodiment, the label 20 includes a first or front side 22 and a second or rear side 24 having a readable information portion 26. The label 20 is affixable to the container 12 by the second side 24 and with the label 20 affixed to the container 12, the readable information portion 26 on the second side 24 is readable through a portion of the container 12. Advantageously, by including readable information on the second or rear side 24 of the label 20, the amount of readable information that can be included on the label 20 is increased by using the previously unused rear side of the label 20.

Referring to FIGS. 1 and 2, a biological specimen collection container 12 for collecting a biological sample 100 of the present disclosure is illustrated. In one embodiment, the container 12 comprises a specimen collection tube 14 and a closure 16. The specimen collection tube 14 may comprise any sample collection tubes or containers. For example, the specimen collection tube 14 may comprise a blood collection tube, a chemistry sample tube, a coagulation sample tube, a hematology sample tube, or other sample tube. In one embodiment, the tube 14 is generally cylindrical and may be made of one or more of the following representative materials: polypropylene, polyethylene terapthalate (PET), glass, or combinations thereof. In other embodiments, the biological specimen collection container 12 may comprise a vessel of a different shape, i.e., other than a cylindrical shape, and, in some instances, may not be a tube. For example, the biological specimen collection container 12 may comprise a collection cup, bag, or other container. In one embodiment, the closure 16 may be made of a resealable elastomeric polymer and additionally may comprise a polymer cap integral to the resealable elastomeric polymer.

The biological specimen collection container 12 may include an open top end 80, a closed bottom end 82, and a sidewall 84 extending therebetween, defusing a container interior 86 adapted to receive a biological specimen 100, such as blood, therein. The closure 16 may cover the open top end 80 of the specimen collection container 12. In some embodiments, the specimen collection container 12 may be a single walled container formed of glass and/or a polymeric composition. In other embodiments, the specimen collection container 12 may include a tube-in-tube configuration in which a second specimen collection container is disposed within the container interior 86. In one embodiment, at least a portion of the container 12 is transparent. For example, the sidewall 84 of the container 12 may be transparent.

In one embodiment, the biological specimen or sample 100 to be collected within a specimen collection tube 14 may be blood. In other embodiments, any other biological specimen or sample may be collected by using one of a blood collection tube, a chemistry sample tube, a coagulation sample tube, a hematology sample tube, or other sample tube.

Referring to FIGS. 1 and 2, the biological sample containment system 10 of the present disclosure includes a labeling system or label 20 for the container 12. In one embodiment, the label 20 includes a first or front side 22 and a second or rear side 24 having a readable information portion 26. The label 20 is affixable to the container 12 by the second side 24 and with the label 20 affixed to the container 12, the readable information portion 26 on the second side 24 is readable through a portion of the container 12. Advantageously, by including readable information on the second side 24 of the label 20, the amount of readable information that can be included on the label 20 is increased by using the previously unused rear side of the label 20. The first side 22 of the label 20 is opposite the second side 24 of the label 20.

In one embodiment, the second side 24 of the label 20 includes a first readable information portion 30 and a second readable information portion 32 located above the first readable information portion 30. In such an embodiment, with the label 20 affixed to the container 12, at least one of the first readable information portion 30 and the second readable information portion 32 is readable through a portion of the container 12. Referring to FIGS. 1 and 2, in one embodiment, at least a part of the first readable information portion 30 is a fill range indicator or fill line indicator 34 and at least a part of the second readable information portion 32 is a barcode 36. Referring to FIG. 2, by having the barcode 36 located above the fill line indicator 34, the barcode 36 can be read by a medical practitioner or lab instrument with a biological sample 100 filled to the fill line indicator 34 within the container 12.

In one embodiment, a barcode 36 may be printed with a variety of different types of inks. For example, the barcode 36 may be printed with a regular ink, a UV fluorescent ink, an IR ink, a metallic ink, a radioactive ink, and/or a water contact ink.

In one embodiment, a thermal energy source may be used to impart information to the label 20. For example, a thermal ink may be used to print information and/or a barcode onto a first side 22 and/or a second side 24 of the label 20.

In one embodiment, the fill line indicator 34 may comprise some form of pre-printed marking or shape specific marking, such as a black solid indicator portion or a cut, cutout, or visible perforation portion. The color, shading, pattern, and shape of such portions may vary as long as each is recognizable by the user. Referring to FIG. 8, in one embodiment, the fill line indicator 34 includes a low fill indicator 60 situated at the bottom boundary of the fill line indicator 34 and a high fill indicator 62 situated at the upper boundary of the fill line indicator 34. In other embodiments, one of either a low fill indicator 60 or high fill indicator 62 may be utilized. The low fill indicator 60 and the high fill indicator 62 set the lower and upper limits for drawing a sample from a sample source, e.g., a patient's venous blood, such that sufficient sample amounts are collected to effectuate certain tests and to effectuate adequate reagent to sample mixing ratios and proper centrifugation considerations or conditions. In another embodiment, the word "fill" or some other word indicative of the indicator's purpose may be displayed in the indicator area. High fill, low fill, and generic fill indicators may comprise boundaries of each limit, or optionally may include a filled or empty space area correlating to a desired fill range. For certain containers, the desired fill range may correlate to the quantity of reagents or additives deployed into the container prior to use or at the point of manufacture to ensure proper sample to additive ration. The fill line indicators may be disposed on a portion of the label 20 such that a user may interpret the level or quantity of sample collected from the patient into the container 12 by looking through a portion of the generally clear sidewall 84 of the container 12.

In one embodiment, the first side 22 of the label 20 includes an outfacing readable information portion 40. The first readable information portion 30, the second readable information portion 32, and/or the outfacing readable information portion 40 of the label 20 may include any information identifying characteristics of the sample and/or container that may be useful to the healthcare practitioner. For example, the information may identify the integrity of the sample, whether the sample has been subjected to appropriate procedures, whether the appropriate amount of sample has been collected, or information that contains product specific information that is important for laboratory instruments or other devices that interact with the container 12.

Furthermore, the information may relate to maximum temperatures that the container and/or sample may be exposed to, the timeframe that the container and/or sample may be used upon manufacture, shipment, or some other event, or the amount of time that has transpired after collection of the sample into the container.

For example, the first readable information portion 30, the second readable information portion 32, and/or the outfacing readable information portion 40 of the label 20 may include fill range indicators, low fill indicators, high fill indicators, hemolysis indicators, time indicators, temperature indicators, or other information identifying characteristics of the sample and/or container that may be useful to the healthcare practitioner.

In one embodiment, at least a part of the first readable information portion 30, at least a part of the second readable information portion 32, and/or at least a part of the outfacing readable information portion 40 comprise electronically readable information and/or machine readable information. For example, in one embodiment, included on a portion of the label 20 is a barcode or some other machine readable data that is unique to each container or optionally unique to a subset of containers. Such information may also be used for storage of additional data associated with a container, such as container manufacturer information, container type, intended draw size information, and the like. In addition, patient-specific, test-specific, or other application-specific information may be stored, e.g., electronically, and associated with the container's unique identifier.

The first readable information portion 30, the second readable information portion 32, and/or the outfacing readable information portion 40 of the label 20 may include a radio frequency identification (RFID) tag which provides information associated with a container. An RFID tag allows for unique identification of the container. Such RFID tags may be passive in nature with an electronic device having some type of reading/scanning mechanism to receive identification information off the tag. In another embodiment, the tag is active in nature in which an electronic device is used to receive a signal generated by or from the tag. In accordance with an embodiment of the invention, the tags may be writeable, readable, or both. With such a system, the need for more conventional type labeling having machine readable or human readable information may be complemented or obviated.

The first readable information portion 30, the second readable information portion 32, and/or the outfacing readable information portion 40 of the label 20 may include information relating to monitoring the maximum temperature to which the label 20 and the container 12 is exposed. In another embodiment, the label 20 may include information relating to measuring the temperature once the label 20 and the container 12 is exposed to light and/or air.

The first readable information portion 30, the second readable information portion 32, and/or the outfacing readable information portion 40 of the label 20 may include information relating to a time and temperature shelf life indicator 54, 56 (FIG. 7) that allows a user to easily observe whether a container has "expired" prior to drawing a sample, testing the sample, or some other point in the sample collection and testing process resulting in fewer redraws or unnecessary or inaccurate testing.

Referring to FIGS. 1 and 6, a portion of the label 20 may include information relating to a mix indicator or inversion indicator 50 that ensures that the appropriate number of mixes and amount of mixing time is performed. Adequate mixing improves sample integrity, quality, and reliability. In one embodiment, an accelerometer may be integrated with the container 12 such that motion representative of mixing may be identified, recorded, and outputted. The output may be in a form that is visually apparent to the user or optionally may be discreet such that the output may be interrogated by a device remote from the tube, i.e., a reading from a hand-held scanner.

Referring to FIGS. 1-8, the first readable information portion 30, the second readable information portion 32, and/or the outfacing readable information portion 40 of the label 20 may include information relating to a hemolysis indicator 52, possibly in the form of a chart or scale. One method for measuring levels of hemolysis, i.e., the breaking of the cell membranes of red blood cells, is visually identifying the color of all or a portion of a blood sample. For example, in many instances, the shade of the serum that resides above the hematocrit for a blood sample is indicative of general qualitative hemolysis levels, such as zero, trace (or slight), moderate, and gross (or severe). Such indication may be displayed by including a color scale on a blood containment device having different hemolysis level terminologies associated with and printed on the hemolysis scale. Some examples of scales/terminologies that can be included to convey for measuring levels of hemolysis are: a 0, +1, +2, and +3 scale; a 0, 1+, 2+, and 3+ scale; a 0, 1, 2, and 3 scale; a 0, +, ++, and +++ scale; or a zero, trace, +, ++, and +++ scale. The color scale for indicating hemolysis ranges from a light yellow to a dark reddish orange. A Pantome color scheme may be chosen to represent variances between the low and high color indicators. Other indications of hemolysis levels may be provided.

Referring to FIG. 1, the first readable information portion 30, the second readable information portion 32, and/or the outfacing readable information portion 40 of the label 20 may include information relating to an order of draw indicator 58.

Referring to FIG. 6, in one embodiment, the second side 24 of the label 20 includes a first information area 91, a second information area 92, a third information area 94, a fourth information area 96, and a fifth information area 98. The information areas may include any of the identifying information described above. In other embodiments, any portion of the label 20 may include any orientation and/or number of information areas configured to provide any of the identifying information described above.

In one embodiment, any portion of the label 20 may include information pertaining to at least one of a manufacture catalog number, identifiable bar code, shelf life, lot identification number, container specific identifier, information specific to a sample intended to be placed or already placed into the container, and/or information specific to a patient in a hospital.

FIGS. 3 and 4 illustrate other exemplary embodiments. The embodiments illustrated in FIGS. 3 and 4 include similar components to the embodiment illustrated in FIGS. 1 and 2, and the similar components are denoted by a reference number followed by the letters A and B. For the sake of brevity, these similar components and the similar steps of using biological sample containment system 10A (FIG. 3) and biological sample containment system 10B (FIG. 4) will not all be discussed in conjunction with the embodiments illustrated in FIGS. 3 and 4.

Referring to FIG. 3, the biological sample containment system 10A includes a label 20A for a container 12A that includes a tear away portion 66. In such an embodiment, the tear away portion 66 may be removed so that a fill line indicator or clear portion 68 is exposed.

Referring to FIG. 4, the biological sample containment system 10B includes a label 20B for a container 12B that includes an invisible bar code label 76 on a rear surface 78 of the label 20B. In such an embodiment, a camera recognition system may be used with the invisible bar code label 76 to read and utilize information.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological sample containment system, comprising:
 a container for containing a biological sample, the container having a top and a bottom disposed opposite the top; and
 a label capable of being affixed to the container, the label comprising:
  a first side;
  a second side, the label affixable to the container by the second side, the second side includes a first readable information portion comprising a fill line indicator and a second readable information portion comprising a barcode indicator above the first readable information portion;
  a first top edge portion, a second bottom edge portion opposite and substantially parallel to the first top edge portion, a third edge portion, and fourth edge portion, the third and fourth edge portions each extending from the first top edge portion to the second bottom edge portion,
  wherein the third edge portion and the fourth edge portion are each longer than the first top edge portion and the second bottom edge portion,
  wherein the barcode indicator is disposed between the fill line indicator and the first top edge portion,
  wherein the top of the container is disposed adjacent the first top edge portion,
  wherein the bottom of the container is disposed adjacent the second bottom edge portion,
  wherein with the label affixed to the container, at least one of the first readable information portion and the second readable information portion is readable through a portion of the container, and
  wherein with the label affixed to the container and with the biological sample filled within the container to the fill line indicator, the second readable information portion is readable through a portion of the container.

2. The biological sample containment system of claim 1, wherein at least a portion of the container is transparent.

3. The biological sample containment system of claim 1, wherein the barcode indicator includes electronically readable information.

4. The biological sample containment system of claim 1, wherein the barcode indicator includes inversion indicator information.

5. The biological sample containment system of claim 1, wherein the barcode indicator includes hemolysis indicator information.

6. The biological sample containment system of claim 1, wherein the barcode indicator includes order of draw indicator information.

7. The biological sample containment system of claim 1, wherein the first side includes an outfacing readable information portion.

8. The biological sample containment system of claim 7, wherein at least a part of the outfacing readable information portion includes a time indicator.

9. The biological sample containment system of claim 7, wherein at least a part of the outfacing readable information portion includes a temperature indicator.

10. The biological sample containment system of claim 7, wherein at least a part of the outfacing readable information portion includes a hemolysis indicator.

11. The biological sample containment system of claim 7, wherein at least a part of the outfacing readable information portion comprises machine readable information.

12. The biological sample containment system of claim 1, wherein the fill line indicator includes a high fill indicator and a low fill indicator.

13. The biological sample containment system of claim 1, wherein the barcode indicator includes information identifying the biological sample.

14. The biological sample containment system of claim 1, wherein the barcode indicator includes information identifying the container.

15. The biological sample containment system of claim 1, wherein with the label affixed to the container and with the container in an upright position, the second readable information portion is above the first readable information portion.

* * * * *